United States Patent [19]
Horney

[11] Patent Number: 5,820,616
[45] Date of Patent: Oct. 13, 1998

[54] ABSORBENT ARTICLE

[75] Inventor: James C. Horney, Cincinnati, Ohio

[73] Assignee: The Procter & Gamble Company, Cincinnati, Ohio

[21] Appl. No.: 892,554

[22] Filed: Jul. 14, 1997

Related U.S. Application Data

[63] Continuation of Ser. No. 563,031, Nov. 27, 1995, abandoned.

[51] Int. Cl.⁶ ............................. A61F 13/15; A61F 13/20
[52] U.S. Cl. ........................................ 604/378; 604/385.1
[58] Field of Search ................................ 604/385.1, 387, 604/378, 386, 389, 390

[56] References Cited

U.S. PATENT DOCUMENTS

| | | | |
|---|---|---|---|
| 2,929,379 | 3/1960 | Poulsen | 128/290 |
| 3,367,334 | 2/1968 | Testa | 128/290 |
| 3,580,252 | 5/1971 | Delort | 128/290 |
| 4,094,316 | 6/1978 | Nathanson | 128/156 |
| 4,097,943 | 7/1978 | O'Connell | 5/335 |
| 4,161,176 | 7/1979 | Harris, II et al. | 128/155 |
| 4,405,310 | 9/1983 | Karami | 604/383 |
| 4,425,130 | 1/1984 | Des Marais | 604/389 |
| 4,576,597 | 3/1986 | Hlaban | 604/390 |
| 4,605,404 | 8/1986 | Sneider | 604/385 |
| 4,657,538 | 4/1987 | Becker et al. | 604/381 |
| 4,765,477 | 8/1988 | Froion et al. | 206/438 |
| 4,806,411 | 2/1989 | Mattingly, III et al. | 428/139 |
| 4,938,756 | 7/1990 | Salek | 604/368 |
| 4,964,857 | 10/1990 | Osborn | 604/395 |
| 5,057,096 | 10/1991 | Faglione | 604/385.1 |
| 5,087,254 | 2/1992 | Davis et al. | 604/386 |
| 5,429,631 | 7/1995 | Grenier | 604/385.1 |
| 5,458,591 | 10/1995 | Roessler et al. | 604/364 |

FOREIGN PATENT DOCUMENTS

| | | |
|---|---|---|
| 5-49660 | 3/1993 | Japan . |
| WO 93/21878 | 11/1993 | WIPO . |
| WO 95/29655 | 11/1995 | WIPO . |

Primary Examiner—John G. Weiss
Assistant Examiner—Ki Yong O
Attorney, Agent, or Firm—Theodore P. Cummings; Steven W. Miller; Jacobus C. Rasser

[57] ABSTRACT

The present invention provides an absorbent article which includes a first absorbent article and a second absorbent article releasably secured to one another. The second absorbent article is folded along its longitudinal edges to provide side flaps which are releasably secured to the garment facing surface of the first absorbent article.

9 Claims, 4 Drawing Sheets

ABSORBENT ARTICLE

This is a continuation of application Ser. No. 08/563,031, filed on Nov. 27, 1995 now abandoned.

FIELD OF THE INVENTION

The present invention relates to absorbent articles such as incontinence pads, sanitary napkins, pantiliners, and the like, and more particularly to absorbent articles having a first absorbent article and a second absorbent article releasably secured to one another.

BACKGROUND OF THE INVENTION

Various absorbent articles such as sanitary napkins and light to medium incontinent devices exist which absorb body exudates such as menses, urine and fecal matter. Disposable products of this type generally comprise a fluid permeable topsheet, a fluid absorbent core, and a fluid impermeable backsheet. Various shapes, sizes and thicknesses of such article have been explored in an attempt to make their use more comfortable and convenient. For example, U.S. Pat. No. 5,389,094, issued to Lavash et al., on Feb. 14, 1995, U.S. Pat. No. 5,383,869, issued to Osborn, III, on Jan. 24, 1995, U. S. Pat. No. 5,382,245, issued to Thompson et al., on Jan. 17, 1995 and U. S. Pat. No. 5,346,486, issued to Osborn III, et al. on Sep. 13, 1994 show numerous shapes, sizes, thicknesses and other alternative variations.

There may be times when a user's needs may be variable or uncertain. At those times, a user may initially employ a first absorbent article, but may need to carry additional absorbent articles in reserve. Such is not always convenient, however. It would be desirable, then, for a user to be able to readily employ a second absorbent article after the first absorbent article has become soiled without having to retrieve the second absorbent article from reserve.

SUMMARY OF THE INVENTION

The present invention provides an absorbent article comprising a first absorbent article and a second absorbent article releasably secured to one another. Each absorbent article includes a periphery comprising a pair of end edges and a pair of longitudinal edges, a body facing surface and a garment facing surface. The first and second absorbent articles comprise liquid pervious topsheets, liquid impervious backsheets joined to the topsheets, and absorbent cores positioned between the topsheets and backsheets.

The second absorbent article may have similar or different geometric dimensions as the first absorbent article, and is positioned beneath the garment facing surface of the first absorbent article. In fact, the second absorbent article can be smaller, of equal size or larger than the first absorbent article in its unfolded state. However, in its folded state, the second absorbent article will always fit on or within the periphery of the first absorbent article. The first and second absorbent articles may have similar or different absorptive capacities.

In a preferred embodiment, the second absorbent article is releasably secured to the first absorbent article by folding the backsheet along its longitudinal edges to create a pair of side flaps which face the garment facing surface of the first absorbent article. The side flaps comprise a securement means for securing the flaps, and thus the second absorbent article, to the garment facing surface of the first absorbent article. Preferably, securement means on the flaps comprises an adhesive. Thus, the second absorbent article remains in a folded configuration until the first absorbent article is removed. Preferably, at removal of the first absorbent article, the flaps of the second absorbent article are unfolded to reveal an absorbent article of smaller, similar, or larger size and geometric configuration than the first absorbent article; note, the second absorbent article can be any size or geometric configuration desired by the manufacturer.

Additionally, at least one grasping member may be disposed on at least the first absorbent article which comprises a tab having a fixed portion joined to the first absorbent article and an extended portion extending outwardly from the periphery of the first absorbent article.

In another embodiment, the grasping members disclosed herein can comprise disposal means positioned on the first surface of the extended portion with a release liner thereon to cover and protect the disposal means prior to use; e.g., protecting an adhesive layer from premature exposure to the air.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene garments or catamenial pads such as pantiliners or other absorbent articles such as incontinence pads, and the like.

Figure 1:
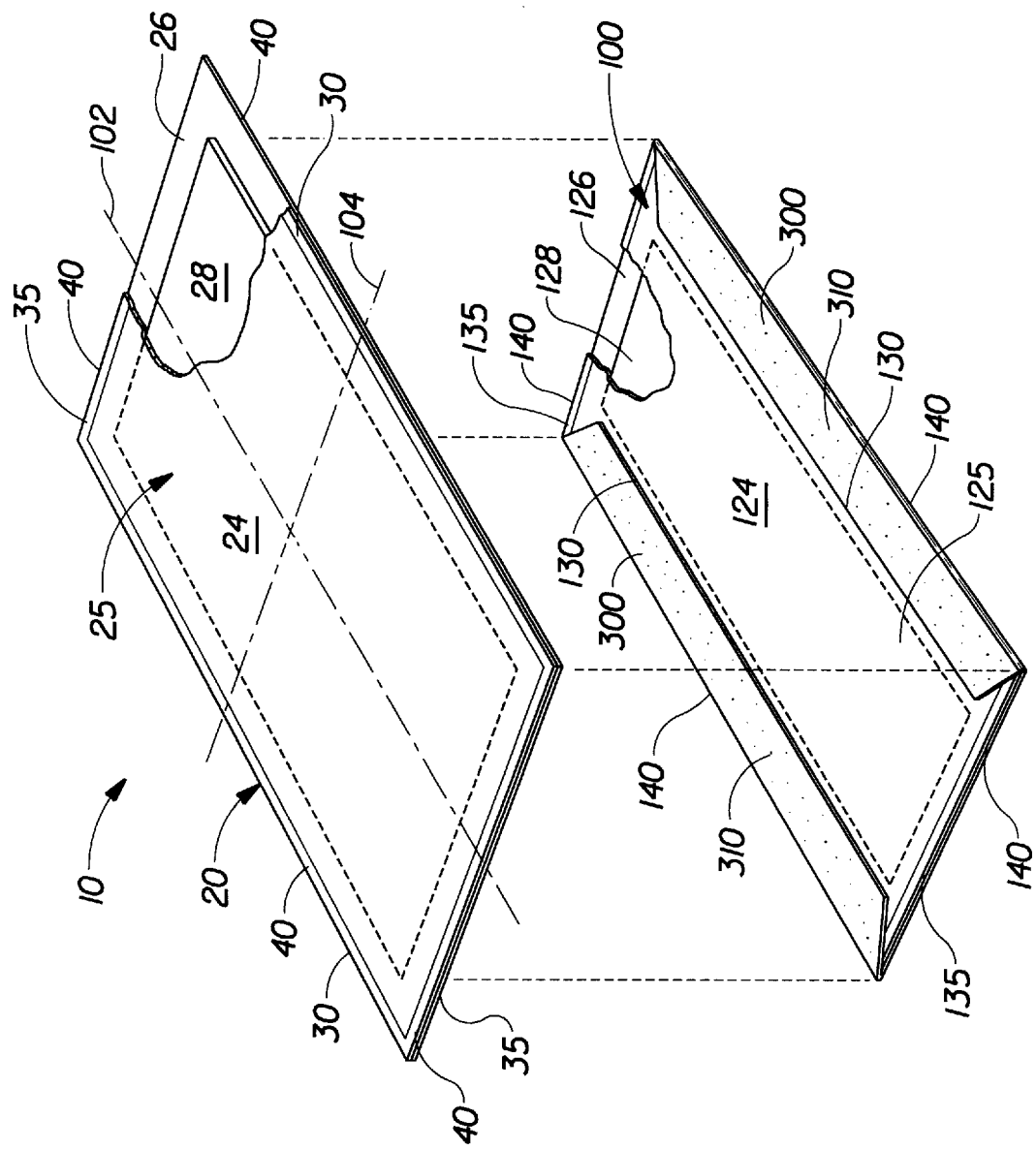
FIG. 1 is an exploded perspective view of the absorbent article of the present invention having portions cut away to reveal underlying structure.

FIG. 1 is an exploded perspective view of an absorbent article 10 of the present invention. The absorbent article 10 comprises a first absorbent article 20 and a second absorbent article 100.

The second absorbent article 100 may have similar or different geometric dimensions than the first absorbent article 20. The second absorbent article 100 is positioned beneath the garment facing surface 27 of the first absorbent article 20. In fact, the second absorbent article 100, when unfolded can be smaller, of equal size or larger than the first absorbent article 20. However, in its folded state, the second absorbent article 100 will always fit on or preferably, within the periphery 40 of the first absorbent article 20. The first and second absorbent articles 20 and 100, may have similar or different absorptive capacities.

The first absorbent article 20 is shown in FIG. 1 with portions of the structure being cut-away to more clearly show the construction of the first absorbent article 20. The first absorbent article 20 preferably comprises a liquid pervious first topsheet 24, a liquid impervious first backsheet 26 joined with the first topsheet 24, and a first absorbent core 28 positioned between the first topsheet 24 and the first backsheet 26.

The first absorbent article 20 has two surfaces, a body-contacting surface, body facing or "body surface" 25 and a garment surface 27 (shown in FIG. 1). The body surface 25 is intended to be worn adjacent to the body of the wearer while the garment surface 27 is on the opposite side and is intended to be placed adjacent to the second absorbent article 100. FIG. 1 also shows that the first absorbent article 20 has a periphery 40 which comprises longitudinal edges 30 and end edges 35.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the first absorbent article 20 in which the topsheet 24 and the backsheet 26 have length and width dimensions generally larger than those of the absorbent core 28. The topsheet 24 and the backsheet 26 extend beyond the edges of the absorbent core 28 to form portions of the periphery 40.

The first absorbent core 28 may be any absorbent means which is capable of absorbing or retaining liquids (e.g., menses and/or urine). As shown in FIG. 1 the first absorbent core 28 has a body surface, a garment surface, side edges, and end edges. The first absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the first absorbent core 28 should, however, be compatible with the design loading and the intended use of the first absorbent article 20. Further, the size and absorbent capacity of the first absorbent core 28 may be varied to accommodate different uses such as incontinence pads, pantiliners, regular sanitary napkins, or overnight sanitary napkins.

Most preferably, the first absorbent core 28 comprises fluid distribution members preferably comprising three basic components: chemically stiffened, twisted, and curled bulking fibers, high surface area fibers, and thermoplastic binder fibers. These fluid distribution members use a high surface fiber to provide capillary pressure (or suction) to the fluid distribution member. These high surface area fibers are generally small and highly conformable. They provide the substrate with capillary pressure well in excess of the capillary pressure found in the bulk-providing chemically stiffened, twisted, and curled fibers alone.

A preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the eucalyptus grandis species. Exemplary fluid distribution members are described in U. S. patent. application Ser. No. 08/382,817 filed Feb. 3, 1995, in the names of J. C. Horney and J. R. Noel, the disclosure of which is incorporated herein by reference.

Exemplary absorbent structures for use as the first absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The first backsheet 26 and the first topsheet 24 are positioned adjacent the garment surface and the body surface, respectively, of the first absorbent core 28 and are preferably joined thereto and to each other by attachment means (not shown) such as those well known in the art. For example, the first backsheet 26 and/or the first topsheet 24 may be secured to the first absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague,. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The first backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The first backsheet 26 prevents the exudates absorbed and contained in the first absorbent core 28 from wetting articles which contact the absorbent articles described herein such as pants, pajamas and undergarments. The first backsheet 26 may thus comprise a woven or nonwoven material, polymeric films such as thermoplastic films of polyethylene or polypropylene, or composite materials such as a film-coated nonwoven material. Preferably, the first backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar, Incorporated of Terre Haute, Ind. under the designation XP-39385. The first backsheet is preferably embossed and/or matte finished to provide a more cloth-like appearance. Further, the first backsheet 26 may permit vapors to escape from the absorbent core 28 (i.e., breathable) while still preventing exudates from passing through the backsheet 26.

The first topsheet 24 is compliant, soft feeling, and non-irritating to the wearers skin. Further, the first topsheet 24 is liquid pervious permitting liquids (e.g., menses and/or urine) to readily penetrate through its thickness. A suitable first topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred first topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred first topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film first topsheet is hydrophilic so as to help liquid to transfer through the topsheet faster than if the body surface was not hydrophilic so as to diminish the likelihood that menstrual fluid will flow off of the first topsheet rather than flowing into and being absorbed by the first absorbent core. In a preferred embodiment, surfactant is incorporated into the polymeric materials of the formed film first topsheet such as is described in U.S. patent application Ser. No. 07/794,745, "Absorbent Article Having A Nonwoven and Apertured Film Coversheet" filed on Nov, 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

The second absorbent article 100 preferably comprises a liquid pervious second topsheet 124, a liquid impervious second backsheet 126 secured to the second topsheet 124, and a second absorbent core 128 positioned between the second topsheet 124 and the second backsheet 126.

The second absorbent article 100 has two surfaces, an absorbent article-contacting surface 125 which becomes a body facing or "body surface" at the removal of the first absorbent article 20 and a garment facing surface 127 (not shown). The second absorbent article 100 is shown in FIG. 1 with portions of the structure being cut-away to more clearly show the construction of the second absorbent article 100. The absorbent article-contacting surface 125 is intended to be worn adjacent to the garment facing surface 27, i.e., the backsheet 26, of the first absorbent article 20. Upon removal of the first absorbent article 20 from a wearer's undergarment, the absorbent article-contacting surface of the second absorbent structure 100 will become the body-facing surface and will thus be worn adjacent to the wearer's body. FIG. 1 also shows that the second absorbent article 100 has a periphery 140 which comprises longitudinal edges 130 and end edges 135.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the second absorbent article 100 in which the second topsheet 124 and the second backsheet 126 have length and width dimensions generally larger than those of the second absorbent core 128. The second topsheet 124 and the second backsheet 126 extend beyond the edges of the second absorbent core 128 to form portions of the periphery 140.

The second absorbent core 128 may be any absorbent means which is capable of absorbing or retaining liquids (e.g., menses and/or urine). As shown in FIG. 1 the second absorbent core 28 has a body surface, a garment surface, side edges, and end edges. The second absorbent core 128 may be manufactured in a wide variety of sizes and shapes (e.g., rectangular, oval, hourglass, dog bone, asymmetric, etc.) and from a wide variety of liquid-absorbent materials commonly used in various absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the second absorbent core 128 may also be varied (e.g., the second absorbent core 128 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the second absorbent core 128 should, however, be compatible with the design loading and the intended use of the second absorbent article 100. Further, the size and absorbent capacity of the second absorbent core 128 may be varied to accommodate different uses such as incontinence pads, pantiliners, regular sanitary napkins, or overnight sanitary napkins. The absorbent capacity of the second absorbent core 128 may be the same as, greater than, or less than the absorbent capacity of the first absorbent core 28 of the first absorbent article 20.

Most preferably, the second absorbent core 128 comprises fluid distribution members comprising three basic components: chemically stiffened, twisted, and curled bulking fibers, high surface area fibers, and thermoplastic binder fibers. These fluid distribution members use a high surface fiber to provide capillary pressure (or suction) to the fluid distribution member. These high surface are fibers are generally small and highly conformable. They provide the substrate with capillary pressure well in excess of the capillary pressure found in the bulk-providing chemically stiffened, twisted, and curled fibers alone.

A preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the eucalyptus grandis species. Exemplary fluid distribution members are described in U. S. patent application Ser. No. 08/382,817 filed Feb. 3, 1995, in the names of J. C. Homey and J. R. Noel, the disclosure of which is incorporated herein by reference.

Exemplary absorbent structures for use as the second absorbent core 128 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The second backsheet 126 and the second topsheet 124 are positioned adjacent the garment surface and the body surface, respectively, of the second absorbent core 128 and are preferably joined thereto and to each other by attachment means (not shown) such as those well known in the art. For example, the second backsheet 126 and/or the second topsheet 124 may be secured to the second absorbent core 128 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL- 1258 or H-203 1. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague,. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The second backsheet 126 is impervious to liquids (e.g., menses and/or urine) and is preferably manufactured from a thin plastic film, although other flexible liquid impervious materials may also be used. The second backsheet 126 prevents the exudates absorbed and contained in the second absorbent core 128 from wetting articles which contact the second absorbent article 100 such as pants, pajamas and undergarments. The second backsheet 126 may thus comprise a woven or nonwoven material, polymeric films such as thermoplastic films of polyethylene or polypropylene, or composite materials such as a film-coated nonwoven material. Preferably, the second backsheet 126 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar, Incorporated of Terre Haute, Ind. under the designation XP-39385. The second backsheet 126 is preferably embossed and/or matte finished to provide a more cloth-like appearance. Further, the second backsheet 126 may permit vapors to escape from the second absorbent core 128 (i.e., breathable) while still preventing exudates from passing through the second backsheet 126.

The second topsheet 124 is compliant, soft feeling, and non-irritating to the wearer's skin. Further, the second topsheet 124 is liquid pervious permitting liquids (e.g., menses and/or urine) to readily penetrate through its thickness. A suitable second topsheet 124 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred second topsheet 124 comprises an apertured formed film. Apertured formed films are preferred for the second topsheet 124 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in the preceding section First Absorbent Article Structure and each of these patents are incorporated herein by reference. The preferred second topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film second topsheet is hydrophilic so as to help liquid to transfer through the topsheet faster than if the body surface was not hydrophilic so as to diminish the likelihood that menstrual fluid will flow off of the second topsheet rather than flowing into and being absorbed by the second absorbent core. In a preferred embodiment, surfactant is incorporated into the polymeric materials of the formed film second topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the second topsheet can be made hydrophilic by treating it with a surfactant such as is described in the above referenced U.S. Pat. No. 4,950,254 issued to Osborn, incorporated herein by reference.

In a preferred embodiment of the present invention, an acquisition layer(s) may be positioned between the topsheets and the absorbent cores of the first absorbent article 20 and the second absorbent article 100, respectively. An acquisition layer may serve several functions including improving wicking of exudates over and into the absorbent core. There are several reasons why the improved wicking of exudates is important, including providing a more even distribution of the exudates throughout an absorbent core and allowing an absorbent article described herein to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent articles disclosed herein having an acquisition layer and a topsheet are more fully described in U.S. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

FIG. 1 shows the second absorbent article 100 comprising a pair of side flaps 300 having securement means 310 disposed thereon by which the second absorbent article 100 is releasably secured to the first absorbent article 20. Preferably, the side flaps 300 comprise at least a portion of the second backsheet 126, and the longitudinal edges 130 which have been folded in over the remainder of the second backsheet 126 during manufacture of the absorbent article, such that the flaps 300, comprising portions of the second backsheet 126, face towards the garment surface 27, i.e., the first backsheet 26, of the first absorbent article 20. The flaps 300 of the second absorbent article 100 which face the garment surface 27 of the first absorbent article 20 have preferably been flattened out to provide an essentially even surface on which to fix a securement means 310 and to provide an adequate surface area for joining the first absorbent article 20 to the second absorbent article 100. It is along these flaps 300 by known securement means 310 in the art, that the first and second absorbent articles 20 and 100 are releasably secured to one-another. Most preferably the securement means 310 is a compatible non-irritating adhesive. Suitable adhesives known in the art are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U. S. Pat. No. 4,9817,697. A preferred adhesive securement means is of the water soluble type. An example of this type is Airflex 401, manufactured by Air Products and Chemicals Incorporated, located in Allentown, Pa.

In most embodiments, the side flaps 300 will also include a portion of the topsheet along with the backsheet which is folded inward to create side flaps 300. While the side flaps 300 may include portions of the absorbent core, it is preferred that they do not as the addition of absorbent core material will make the flaps bulky, stiff and thus difficult to fold. Therefore, it is preferred that the side flaps not include any portion of the absorbent core.

In an alternative embodiment, the absorbent article 100 comprises a pair of flaps comprising at least a portion of the backsheet and the end edges 135 which have been folded in over the remaining portion of the backsheet. The end edges 135 may be folded towards the body-contacting surface 125 of the second absorbent article 100 such that the first absorbent article 20 would be releasably secured to the second absorbent article 100 via the longitudinal flaps 300 and end edge flaps, respectively.

In a preferred embodiment, the second absorbent article 100 is releasably secured to the first absorbent article 20 by flaps 300 which have been folded in over the backsheet to face the garment facing surface 27 of the first absorbent article 20. Flaps 300 comprise a securement means 310 for securing the flaps 300, and thus the second absorbent article 100, to the garment facing surface 27 of the first absorbent article 20. Preferably, securement means 310 on the flaps 300 comprises an adhesive. The securement means maintains the second absorbent article 100 remains in a folded configuration until the first absorbent article 20 is removed. Preferably, at removal of the first absorbent article 20, the second absorbent article 100 is then unfolded to reveal the entire structure. The second absorbent article may be smaller, similar, or larger in size and geometric configuration than the first absorbent article 20. The second absorbent article 100 can be any size or geometric configuration desired by the manufacturer.

Figure 2:
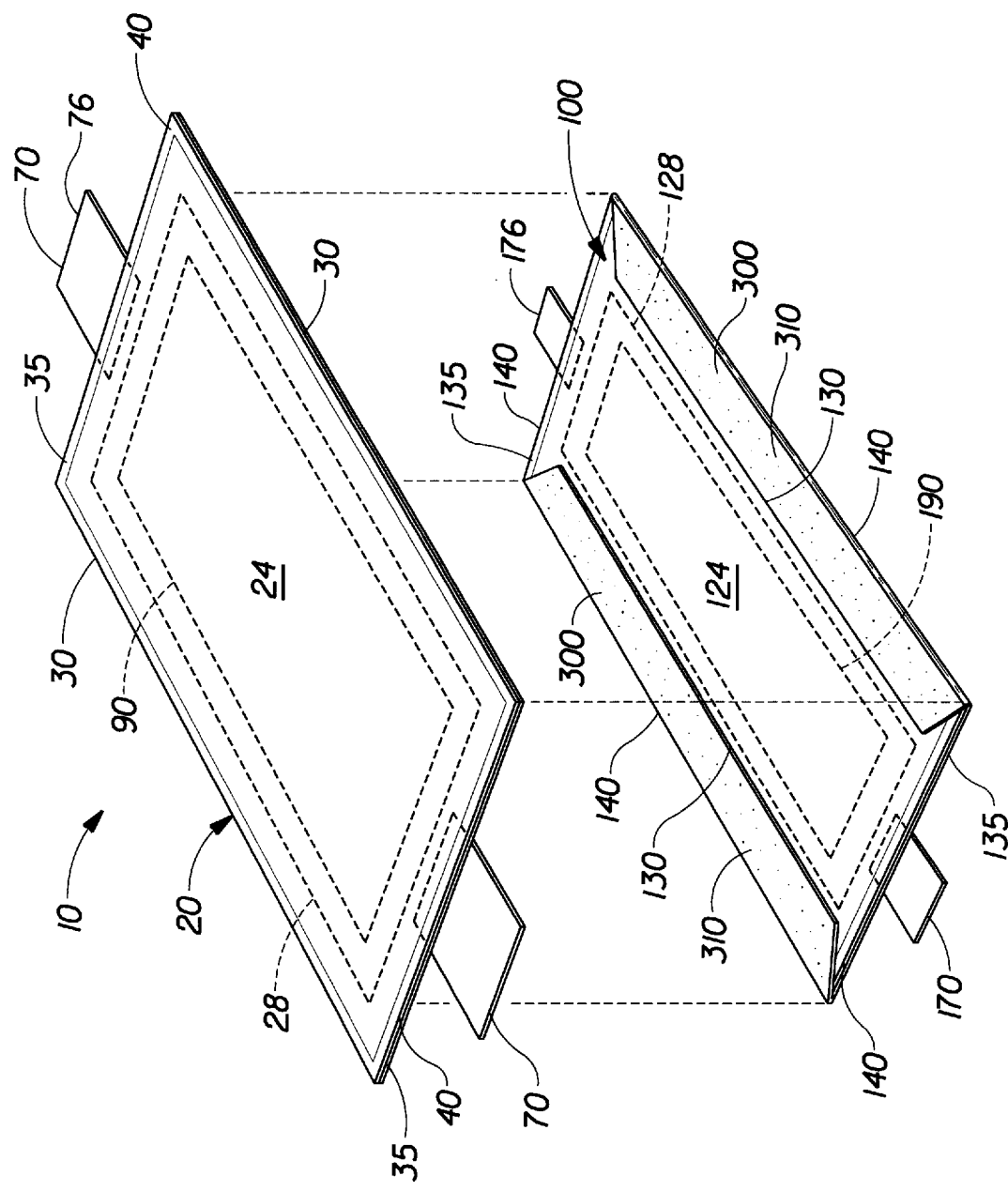
FIG. 2 is an exploded perspective view of another embodiment of an absorbent article of the present invention.
Figure 5:
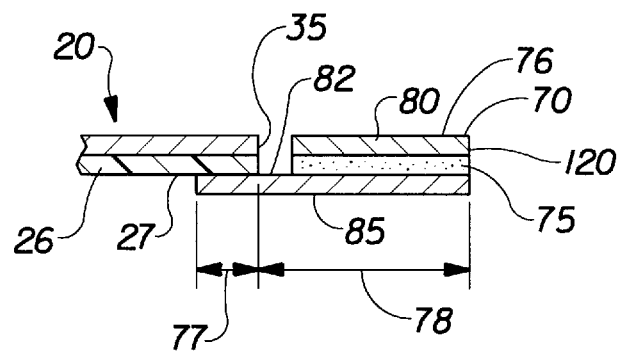
FIG. 5 is a fragmentary side view of the first absorbent article showing the grasping member.

Referring now to FIG. 2 the first absorbent article 20 preferably comprise at least one grasping member 70. Grasping member 70 preferably comprises a tab 76. Referring now to FIG. 5, the tab 76 has a first surface 82 facing the wearer and a second surface 85 facing the second absorbent article. The tab 76 is joined to the backsheet 26 to create a fixed portion 77 (i.e., that portion of the tab 76 joined to the first absorbent article during manufacture). The tab 76 has another element which is the extended portion 78 which is that portion of the tab 76 which extends outwardly beyond the periphery of the first absorbent article and that is grasped by the user to separate the first absorbent article 20 from the second absorbent article 100. The distal end 120 of the tab 76 preferably has rounded corners to eliminate the possibility of harsh corner edges contacting the wearer's skin.

As shown in FIGS. 2 and 5 the tab 76 is joined to the first absorbent article such that the extended portion 78 extends outwardly from an end edge 35 of the first absorbent article. Alternatively, the tab 76 may be joined to the first absorbent article such that the extended portion 78 of the tab 76 extends outwardly from one of the longitudinal edges.

In the embodiments shown in FIGS. 2 and 5, the fixed portion 77 is joined to the outer surface of the first backsheet 26. Alternatively, the fixed portion 77 may be joined to the first absorbent article by positioning the fixed portion 77 between the topsheet and the backsheet. While the fixed portion 77 may be joined directly to the body contacting surface of the topsheet, this is not preferred as the tab 76 may interfere with the fluid handling properties of the topsheet and may also be subjected to soiling. The tab 76 may extend from the absorbent core or at least may have its fixed portion 77 located between the topsheet and backsheet, and thus extend outwardly therefrom.

Tab 76 will most preferably comprise polymer, but can alternatively comprise paper and/or cloth. Furthermore, the tab 76 can be an extension of the first backsheet 26, first topsheet 24 or first core 28. In alternative embodiments the tab 76 can be positioned on the longitudinal edges 30 and 130 of the first and second absorbent articles 20 and 100, respectively.

The tab 76 may also comprise a disposal means 75 joined to the first surface 82 of the extended portion 78. The disposal means 75 allows the first absorbent article 20 to be secured in a configuration that provides convenient disposal of the first absorbent article 20 and reduces leakage of liquid and/or solid exudates. Thus, the disposal means 75 may be any structure that allows the first absorbent article 20 to be folded or rolled up into a configuration for disposal and secured in that configuration. For example, the disposal means 75 may comprise a number of different elements positioned on the first surface 82 of the tab 76 such as an adhesive, or any other compatible element known to those of skill in the art. Compatible adhesives for the disposal means 75 can be, but are not limited to, Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Release member 80 protects the adhesive disposal means 75 from drying out prior to use. A suitable release member is described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

In an alternative embodiment, the disposal means 75 is a mechanical loop or hook type as disclosed in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989 and are incorporated herein by preference. For a hook disposal means 75, loops will on the backsheet and optimally placed to receive the hooks. For a loop disposal means 75, hooks will be on the backsheet and optimally placed to receive the loops.

The second absorbent article 100 may also comprise at least one tab 176 for the same purpose, made up of the same materials, and positioned on second absorbent article 100 just as tab 76 is positioned on the first absorbent article 20. For example, FIG. 2 shows tab 176 fitted and positioned to the second absorbent article 100 as tab 76 is fitted and positioned on the first absorbent article 20.

FIGS. 1 and 2 show the absorbent article comprising a first absorbent article 20 and a second absorbent article 100. Note, in all embodiments of the present invention as many absorbent articles as desired can be included. A preferable range of absorbent articles to include is from 2 to 15.

Figure 3:
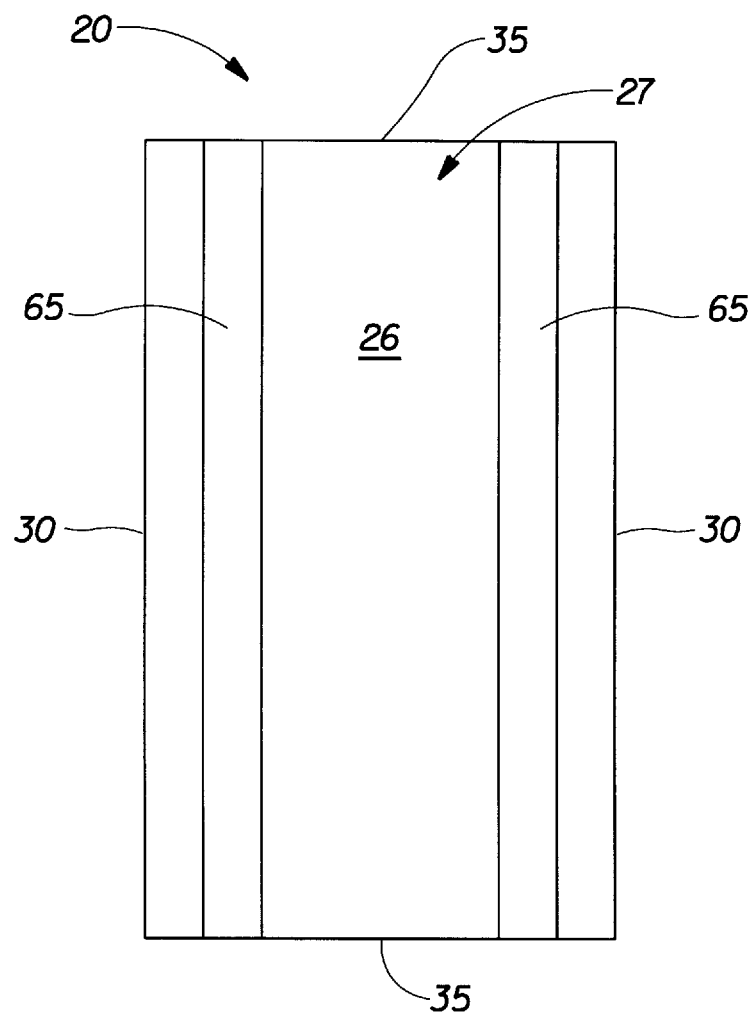
FIG. 3 is a plan view of the garment facing surface of the first absorbent article of the present invention.

FIG. 3 shows the first absorbent article 20 having a release means 65 on the garment surface 27, i.e., on the first backsheet 26. The release means 65 serves as the point of adhesive between the first absorbent article 20 and the second absorbent article 100. In another embodiment the release means 65 is a release liner compatible with the adhesive securement means 310 disclosed herein. The adhesive securement means 310 will most preferably be aligned with the release liner 65 and be releasably affixed thererto. This spacial alignment is such that the release liner 65 will most preferably house the entire adhesive surface area of the adhesive securement means 310. Suitable release liners are described in U. S. Pat. No. 4,917,697 and 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Note, the release means 65 can comprise one piece of material for its purpose, but preferably will comprise more than one piece of material shown in FIG. 3. The release means 65 on the first absorbent article 20 can be placed on the garment surfaces of the backsheets of all subsequent absorbent articles on which receive the securement means from a subsequent absorbent article. In other preferred embodiments, the securement means on the folds of an absorbent article will adhere directly to the backsheet and garment surface of the absorbent article to which it is to be connected; i.e., securement means will not adhere to release means.

In an alternative embodiment, the release means 65 can comprise mechanical fasteners; for example, hooks and/or loops which receive a mechanical fastener from the securement means 310. Any mechanical fasteners known in the art are suitable for the invention disclosed herein, and examples include those of mechanical closure systems disclosed in U. S. Pat. No. 4,869,724 issued to Scripps on Sep. 9, 1989; U. S. Pat. No. 4,848,815 issued to Scripps on Jul. 11, 1989 and the two-point securement system described in U. S. Pat. No. 5,242,436 issued to Weil, Buell, Clear, and Falcone on Sep. 7, 1993 each of which are incorporated herein by reference. Most preferably, with each of these mechanical securement systems, the release means 65 herein will comprise that element suited for reception, for example, loops and, the securement means 310 will comprise that element suited for adhesion, for example, hooks.

Figure 4:
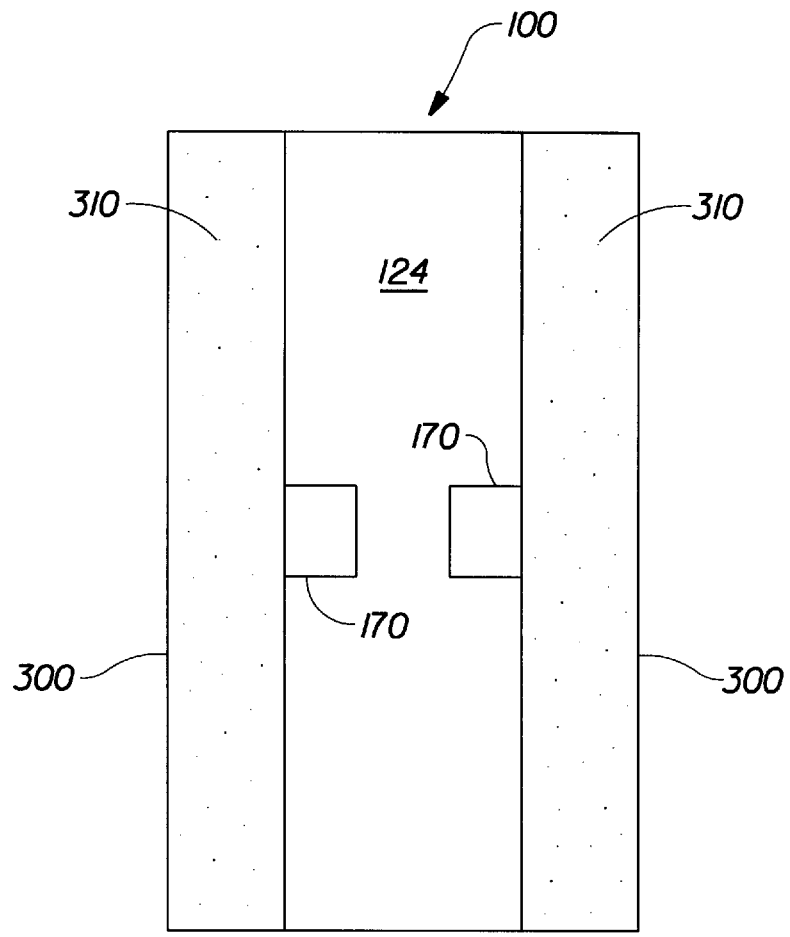
FIG. 4 is a plan view of another embodiment of the second absorbent article showing the unfolding means.

FIG. 4 discloses an alternative embodiment for the second absorbent article 100. The second absorbent article 100 may comprise unfolding means 170 which preferably comprises tabs to unfold the second absorbent article 100 after the first absorbent article 20 has been removed. At such unfolding, the flaps 300 are turned down to face a user's undergarment.

Alternatively, the securement means 3 10 which previously held the first absorbent article 20 may be used to additionally secure the absorbent articles in place in a user's undergarment. In a most preferred embodiment, the second absorbent article 100 comprises panty fastening adhesive or attachment means (not shown) which is placed on the garment facing surface 127 to secure the absorbent article 10 to a user's undergarment. In an embodiment in which there are more than two absorbent articles, the lower most absorbent article will be that absorbent article that comprises attachment means on its garment facing surface to secure the entire embodiment to a user's undergarment.

The unfolding means 170 is preferably a tab and most preferably comprises polyethylene, but can alternatively comprise paper and/or cloth. Alternatively, the second absorbent article 100 may not comprise unfolding means 170. Instead, a user can slide a finger between a flap 300 and the topsheet 124 to release the flap 300. Then, after release, a user can bend a flap 300 to the position wherein the securement means 310 portion of the flap 300 is now in the garment-facing direction of the article 100, i.e., the securement means is flipped down to face a wearer's undergarment.

Preferably, the absorbent article 10 is held in place in a user's undergarment by attachment means (not shown) located on the garment surface 127 of the second backsheet 126 of the second absorbent article 100. Preferably, the absorbent article 10, comprising the first absorbent article 20 and the second absorbent article 100 is placed in the user's undergarment or panty and secured thereto by a fastener located on the garment surface 127 of the second backsheet 126 of the second absorbent article 100 such as an adhesive. Most preferably, the attachment means is an adhesive which secures the second absorbent article 100 and thus the first absorbent article 20 when the first absorbent article 20 is releasably secured to the second absorbent article 100. Thus, a portion or all of the garment surface 127 of the second backsheet 126 comprises an adhesive attachment means. Any adhesive or glue used in the art for such purposes can be used for the adhesive attachment means herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the second absorbent article 100 is placed in use, the pressure-sensitive adhesive attachment means is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

After the first absorbent article 20 has been soiled, the user removes the absorbent article 20 from his/her undergarment via the grasping member 70. At removal, the absorbent article 20 is peeled or pulled away from the second absorbent article 100 preferably in a front to back motion. Upon removal of the absorbent article 20, the adhesive disposal means 75 is exposed. The adhesive disposal means 75 most preferably attaches to the first backsheet 26 of the absorbent article 20 thus producing an absorbent article 20 that is folded at or near its lateral axis, or it is trifolded along two axis parallel to the lateral axis, or is rolled in a circular configuration. The folded and sealed absorbent article 20 has its first backsheet 26 as the exterior surface, and its first topsheet 24 as the interior and soiled surface. The absorbent article 20 is now ready for disposal and remains sealed, and thereby at least partially reduces liquid, solid and vapor leakage.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
   a first absorbent article having a periphery comprising a pair of end edges and a pair of longitudinal edges, a body facing surface and a garment facing surface, said first absorbent article comprising a liquid pervious first topsheet, a liquid impervious first backsheet joined to said first topsheet, and a first absorbent core positioned between said first topsheet and said first backsheet;
   a second absorbent article having a periphery comprising a pair of end edges and a pair of longitudinal edges, a body facing surface and a garment facing surface, said second absorbent article comprising a liquid pervious second topsheet, a liquid impervious second backsheet joined to said second topsheet, a second absorbent core positioned between said second topsheet and said second backsheet, and a pair of side flaps comprising at least a portion of said second backsheet, said side flaps being folded in over said second topsheet and said side flaps being releasably secured to said first backsheet of said first absorbent article; and
   a securement means positioned onto each said flap for directly attaching said second absorbent article to said first absorbent article, such that at least a portion of said first backsheet and at least a portion of said second backsheet are releasably and directly secured to one-another by said securement means.

2. The absorbent article of claim 1 wherein said side flaps are releasably secured to said first backsheet of said first absorbent article with an adhesive.

3. The absorbent article of claim 1 wherein said second backsheet of said second absorbent article comprises a panty fastening adhesive and a release liner joined to said panty fastening adhesive.

4. The absorbent article of claim 1 wherein said side flaps each comprise at least one unfolding means.

5. The absorbent article of claim 1 comprising at least one grasping member, disposed on at least said first absorbent article, comprising a tab having a fixed portion joined to said first absorbent article and an extended portion connected to said fixed portion and extending outwardly from said periphery of said first absorbent article, said extended portion comprising a first surface and a second surface.

6. The absorbent article of claim 5 wherein said extended portion extends outwardly from one of said end edges of said first absorbent article.

7. The absorbent article of claim 5 further comprising disposal means joined to said first surface of said extended portion of said grasping member for allowing the first absorbent article to be secured in a configuration that provides convenient disposal of said first absorbent article.

8. The absorbent article of claim 7 wherein said disposal means comprises an adhesive layer.

9. The absorbent article of claim 8 further comprising a release member joined to said adhesive layer.

* * * * *